(12) United States Patent
Burks et al.

(10) Patent No.: US 10,493,449 B2
(45) Date of Patent: Dec. 3, 2019

(54) LOADING TOOL FOR A MULTI-WELL CHROMATOGRAPHY FILTER PLATE

(71) Applicant: Halliburton Energy Services, Inc., Houston, TX (US)

(72) Inventors: Jody Marie Burks, Spring, TX (US); Christopher Ray Bell, Humble, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 132 days.

(21) Appl. No.: 15/520,373

(22) PCT Filed: Nov. 19, 2014

(86) PCT No.: PCT/US2014/066309
§ 371 (c)(1),
(2) Date: Apr. 19, 2017

(87) PCT Pub. No.: WO2016/080975
PCT Pub. Date: May 26, 2016

(65) Prior Publication Data
US 2017/0320055 A1    Nov. 9, 2017

(51) Int. Cl.
*B01L 3/00* (2006.01)
*G01N 35/10* (2006.01)
(Continued)

(52) U.S. Cl.
CPC .......... *B01L 3/50255* (2013.01); *B01D 15/14* (2013.01); *B01L 3/502707* (2013.01);
(Continued)

(58) Field of Classification Search
CPC ... B01D 15/14; B01L 3/50255; B01L 3/5027; B01L 3/502707; B01L 2200/02;
(Continued)

(56) References Cited

U.S. PATENT DOCUMENTS 2,284,956 A * 6/1942 Gardner ................. B21D 37/10
269/13
5,290,521 A * 3/1994 DeStefano, Jr. .......... B01L 3/02
422/563
(Continued)

OTHER PUBLICATIONS

International Search Report and Written Opinion, Application No. PCT/US2014/066309; 10 pgs, dated Jul. 23, 2015.
(Continued)

*Primary Examiner* — Christopher Adam Hixson
(74) *Attorney, Agent, or Firm* — Baker Botts L.L.P.

(57) ABSTRACT

In accordance with some embodiments of the present disclosure, a loading tool for a multi-well chromatography filter plate is disclosed. The loading tool may include a top plate and a bottom plate slidably coupled to the top plate. The top plate may include a plurality of wells for holding a material, a rail located along a side of the top plate, and a notch formed in the rail. The bottom plate may include a plurality of funnels extending from the bottom plate, each of the plurality of funnels corresponding to one of the plurality of wells, a track located along a side of the bottom plate to receive the rail located on the top plate, and a pathway formed in the track to receive the notch such that the notch and the pathway limit movement of the top plate relative to the bottom plate.

9 Claims, 5 Drawing Sheets

(51) Int. Cl.
  *B01D 15/14* (2006.01)
  *G01N 30/16* (2006.01)
  *G01N 30/88* (2006.01)

(52) U.S. Cl.
  CPC .............. *B01L 3/52* (2013.01); *G01N 30/16* (2013.01); *G01N 35/1011* (2013.01); *B01L 2200/02* (2013.01); *B01L 2200/025* (2013.01); *B01L 2300/069* (2013.01); *B01L 2300/0829* (2013.01); *B01L 2400/0493* (2013.01); *G01N 2030/8854* (2013.01)

(58) Field of Classification Search
  CPC ....... B01L 2200/025; B01L 2300/0829; G01N 35/1011
  See application file for complete search history.

(56) References Cited

U.S. PATENT DOCUMENTS

| | | | | |
|---|---|---|---|---|
| 5,595,127 | A * | 1/1997 | Eustace | A47B 47/025 108/109 |
| 6,165,417 | A * | 12/2000 | Swierkowski | B01L 3/0268 422/504 |
| 2002/0131905 | A1 | 9/2002 | Cordill | |
| 2002/0179520 | A1 * | 12/2002 | Madden | B01D 61/18 210/416.1 |
| 2004/0031686 | A1 | 2/2004 | Foret et al. | |
| 2005/0056540 | A1 | 3/2005 | Ramstad et al. | |
| 2006/0230575 | A1 * | 10/2006 | Quinn | E05D 15/0647 16/87.2 |
| 2009/0109433 | A1 * | 4/2009 | Matsumoto | G01N 21/03 356/244 |
| 2011/0286897 | A1 * | 11/2011 | Uschkureit | B01L 3/5085 422/553 |
| 2013/0065771 | A1 | 3/2013 | Oroskar et al. | |

OTHER PUBLICATIONS

MultiScreen® Column Loader, Millipore Corporation Product Brochure, 1 pg, 1996.
Titan 24 Well Resin Loader™, Radleys Discovery Technologies Product Brochure, 2 pgs, 2002.
FlexChem® Peptide Synthesis System, SciGene Corporation Product Brochure, 2 pgs, 2005.
Manual Microplate Bead Loader, BioSpec Products, 2 pgs, 2014.

* cited by examiner

US 10,493,449 B2

LOADING TOOL FOR A MULTI-WELL CHROMATOGRAPHY FILTER PLATE

RELATED APPLICATIONS

This application is a U.S. National Stage Application of International Application No. PCT/US2014/066309 filed Nov. 19, 2014, which designates the United States, and which is incorporated herein by reference in its entirety.

TECHNICAL FIELD

The present disclosure relates generally to chromatography analysis operations and, more particularly, a loading tool for a multi-well chromatography filter plate and methods of using the loading tool.

BACKGROUND

Chromatography analysis techniques may be used to analyze the separation of mixtures for various research and/or industrial purposes in industries such as oil and gas, pharmaceuticals, and biotechnology. Chromatography may be used to separate the components of a mixture and determine the proportions of each component in the mixture. High throughput chromatography may involve the use of filter plates containing multiple wells that may be analyzed at the same time using the chromatography test apparatus or that may be used to prepare concentrated solution(s) of a component or components.

For example, in the oil and gas industry, materials from a subterranean operation, such as drill cuttings or other particulate material, may be suspended or packed in a drilling fluid and may provide useful information about the subterranean formation from which they came. For example, such experiments examine the chemistries, performance, or characteristics of materials such as small amounts of the formation fluids (e.g., oil, water, etc.) of interest that are present in the formation. The permeability, porosity, rock composition, and/or other properties of the subterranean formation also may be of interest. Chromatography may be used to identify the properties of the materials and provide information for use in designing a subterranean operation and/or selecting materials for use in a subterranean operation.

BRIEF DESCRIPTION OF THE DRAWINGS

For a more complete understanding of the present disclosure and its features and advantages, reference is now made to the following description, taken in conjunction with the accompanying drawings, in which.

DETAILED DESCRIPTION

A loading tool for a multi-well chromatography filter plate and related systems and methods are disclosed. A multi-well chromatography filter plate may include multiple wells, e.g., from two wells to hundreds of wells, that may be loaded with material for testing. Each well may be loaded individually by a user using a scoop and a funnel. Alternatively, the multi-well chromatography filter plate may be loaded by using a loading tool. The loading tool may be formed of a top plate and a bottom plate. The top plate may include multiple wells which may be loaded with solid material for use in chromatography or assay testing. The bottom plate may include multiple funnels that may align with the wells of the multi-well chromatography filter plate. A user may fill the wells of the top plate with solid material while the loading tool is in a loading position and then may place the loading tool over the multi-well chromatography filter plate and move the top plate from the loading position to an empty position to allow the solid material to flow from the top plate, through the funnels, and into the wells of the filter plate. The use of a loading tool may provide more efficient multi-well chromatography filter plate loading and reduce the potential for user error. Additionally, the use of the loading tool may reduce variability in the packing and amount of solid material loaded into the wells of the multi-well chromatography filter plate by providing a consistent flow rate into each well of the multi-well chromatography filter plate through the use of funnels. Further the use of the loading tool may allow a solid material to be introduced into a pre-loaded liquid material. Accordingly, a loading tool and method of use may be designed in accordance with the teachings of the present disclosure and may have different designs, configurations, and/or dimensions according to a particular application. Embodiments of the present disclosure and its advantages are best understood by referring to FIGS. 1 through 5, where like numbers are used to indicate like and corresponding parts.

Figure 1:
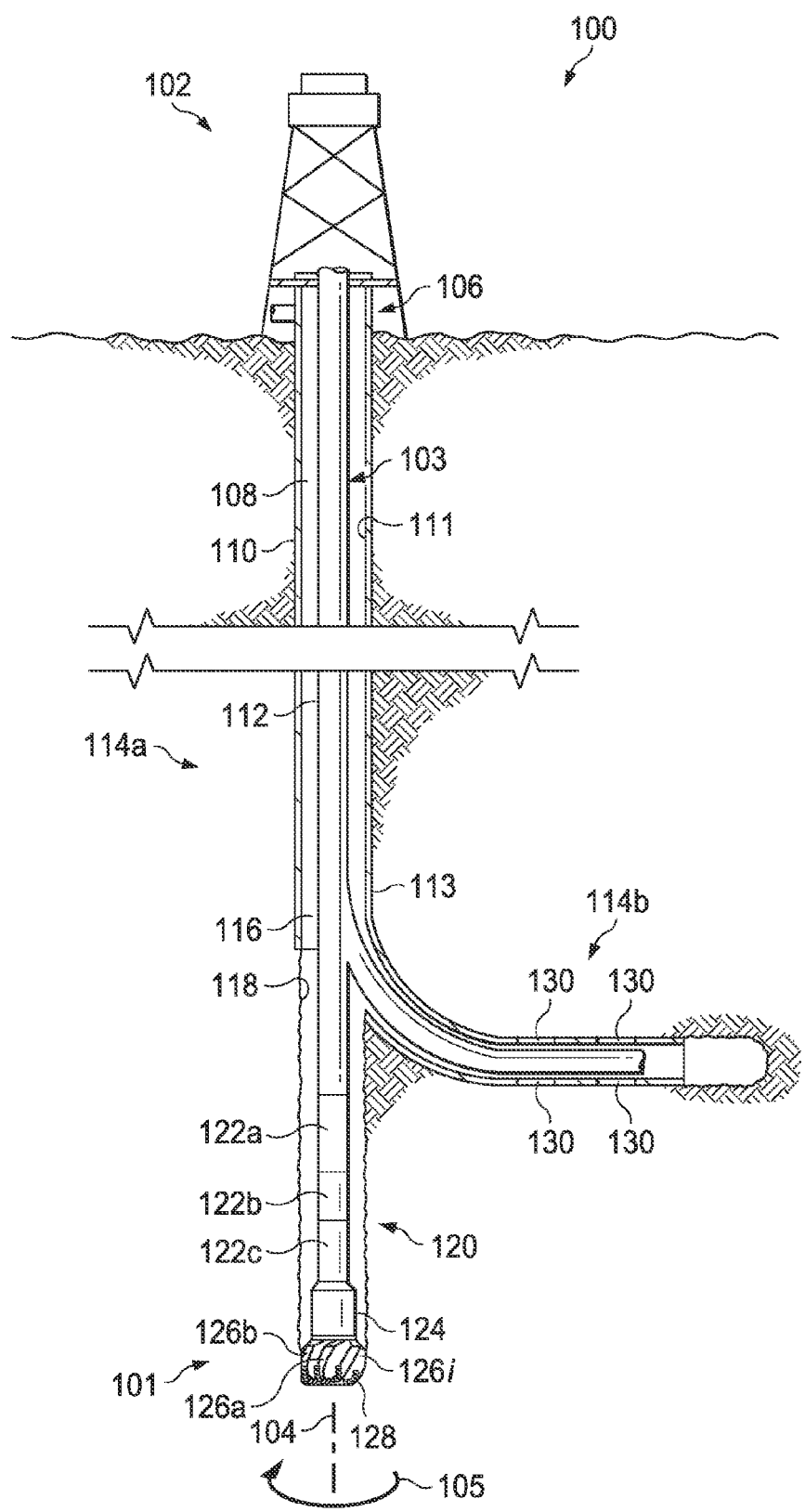
FIG. 1 illustrates an elevation view of an example embodiment of drilling system.

FIG. 1 illustrates an elevation view of an example embodiment of a drilling system. Drilling system 100 may include well surface or well site 106. Various types of drilling equipment such as a rotary table, drilling fluid pumps and drilling fluid tanks (not expressly shown) may be located at well surface or well site 106. For example, well site 106 may include drilling rig 102 that may have various characteristics and features associated with a "land drilling rig." However, downhole drilling tools incorporating teachings of the present disclosure may be satisfactorily used with drilling equipment located on offshore platforms, drill ships, semi-submersibles and drilling barges (not expressly shown).

Drilling system 100 may also include drill string 103 associated with drill bit 101 that may be used to form a wide variety of wellbores or bore holes such as generally vertical wellbore 114a or generally horizontal 114b wellbore or any combination thereof. Various directional drilling techniques and associated components of bottom hole assembly (BHA) 120 of drill string 103 may be used to form horizontal wellbore 114b. For example, lateral forces may be applied to BHA 120 proximate kickoff location 113 to form generally horizontal wellbore 114b extending from generally vertical wellbore 114a. The term "directional drilling" may be used to describe drilling a wellbore or portions of a wellbore that extend at a desired angle or angles relative to vertical. The desired angles may be greater than normal variations associated with vertical wellbores. Direction drilling may also be described as drilling a wellbore deviated from vertical. The term "horizontal drilling" may be used to include drilling in a direction approximately ninety degrees (90°) from vertical. "Uphole" may be used to refer to a portion of wellbore 114 that is closer to well surface 106. "Downhole" may be used to refer to a portion of wellbore 114 that is further from well surface 106.

BHA 120 may be formed from a wide variety of components configured to form wellbore 114. For example, components 122a, 122b, and 122c of BHA 120 may include, but are not limited to, drill bits (e.g., drill bit 101), coring bits, drill collars, rotary steering tools, directional drilling tools, downhole drilling motors, reamers, hole enlargers or stabilizers. The number and types of components 122 included in BHA 120 may depend on anticipated downhole drilling conditions and the type of wellbore that will be formed by drill string 103 and rotary drill bit 101. BHA 120 may also include various types of well logging tools (not expressly shown) and other downhole tools associated with directional drilling of a wellbore. Examples of logging tools and/or directional drilling tools may include, but are not limited to, acoustic, neutron, gamma ray, density, photoelectric, nuclear magnetic resonance, rotary steering tools and/or any other commercially available well tool. Further, BHA 120 may also include a rotary drive (not expressly shown) connected to components 122a, 122b, and 122c and which rotates at least part of drill string 103 together with components 122a, 122b, and 122c.

Wellbore 114 may be defined in part by casing string 110 that may extend from well surface 106 to a selected downhole location. Portions of wellbore 114, as shown in FIG. 1, that do not include casing string 110 may be described as "open hole." Various types of drilling fluid may be pumped from well surface 106 through drill string 103 to attached drill bit 101. The drilling fluids may be directed to flow from drill string 103 to respective nozzles passing through rotary drill bit 101. The drilling fluid may be circulated back to well surface 106 through annulus 108. In open hole embodiments, annulus 108 may be defined in part by outside diameter 112 of drill string 103 and inside diameter 118 of wellbore 114. In embodiments using casing string 110, annulus 108 may be defined by outside diameter 112 of drill string 103 and inside diameter 111 of casing string 110.

Drilling system 100 may also include rotary drill bit ("drill bit") 101. Drill bit 101 may include one or more blades 126 that may be disposed outwardly from exterior portions of rotary bit body 124 of drill bit 101. Blades 126 may be any suitable type of projections extending outwardly from rotary bit body 124. Drill bit 101 may rotate with respect to bit rotational axis 104 in a direction defined by directional arrow 105. Blades 126 may include one or more cutting elements 128 disposed outwardly from exterior portions of each blade 126. Blades 126 may also include one or more depth of cut controllers (not expressly shown) configured to control the depth of cut of cutting elements 128. Blades 126 may further include one or more gage pads (not expressly shown) disposed on blades 126. Drill bit 101 may be designed and formed in accordance with teachings of the present disclosure and may have many different designs, configurations, and/or dimensions according to the particular application of drill bit 101.

BHA 120 may also include a stimulation assembly (not expressly shown). The stimulation assembly may be configured to create perforations 130 in casing string 110. Perforations 130 may allow for other stimulation activities, such as fracturing, acidizing, matrix acidizing, or any other suitable stimulation activity to be performed in wellbore 114. During stimulation activities, fluid may be injected into wellbore 114. The fluid may travel through wellbore 114 and may exit wellbore 114 at perforations 130.

In some subterranean operations, it may be advantageous to determine properties of the formation and reservoir near or surrounding wellbore 114 and/or perforations 130, as disclosed in further detail with respect to FIGS. 2 and 3. For example, information about the formation and/or reservoir may be used to determine the compatibility of a fracturing fluid with the formation, the compatibility of the fracturing fluid with the water and chemical content of the formation, and the effect the use of the fracturing fluid may have on oil productivity and/or fluid recovery from the reservoir. Chromatography, including high-throughput chromatography, may be used to determine the fluid and mineralogy properties of the formation and/or reservoir. High throughput chromatography techniques may use multi-well chromatography filter plates or individual column chromatography arrays or similar experimental setups. To perform an exemplary chromatography or other type of analysis, the wells of the multi-well chromatography filter plate may be filled with solid material (e.g., sand, formation cuttings, chromatography resins, and proppants) for testing. The solid material may be added to an empty well of the multi-well chromatography filter plate or added to a multi-well chromatography filter plate where the wells of the multi-well chromatography filter plate have been pre-loaded with a liquid or a different solid material. Filling the wells individually may be time consuming and introduce well-to-well variability. As such, a tool for loading multi-well chromatography filter plates designed according to the present disclosure may improve accuracy and efficiency of chromatography testing by providing more efficient multi-well chromatography filter plate loading, reducing the potential for user error, and reducing variability in the packing and amount of solid material loaded into the wells of the multi-well chromatography filter plate.

Figure 2A:
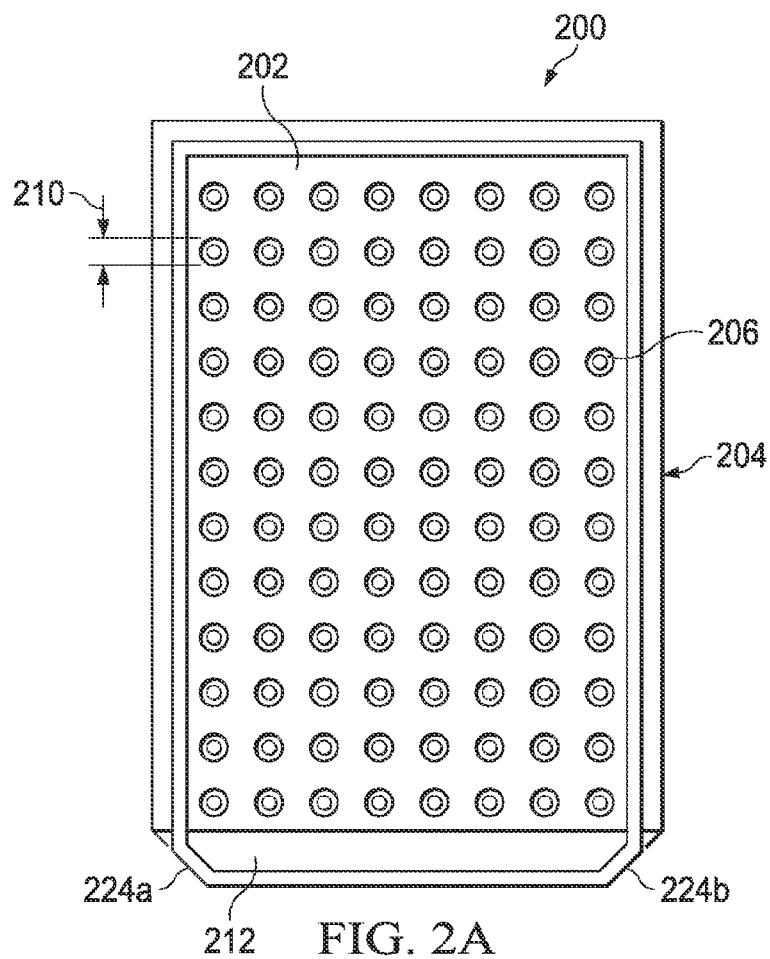
FIGS. 2A-2D illustrate views of an exemplary loading tool for a multi-well chromatography filter plate.
Figure 2B:
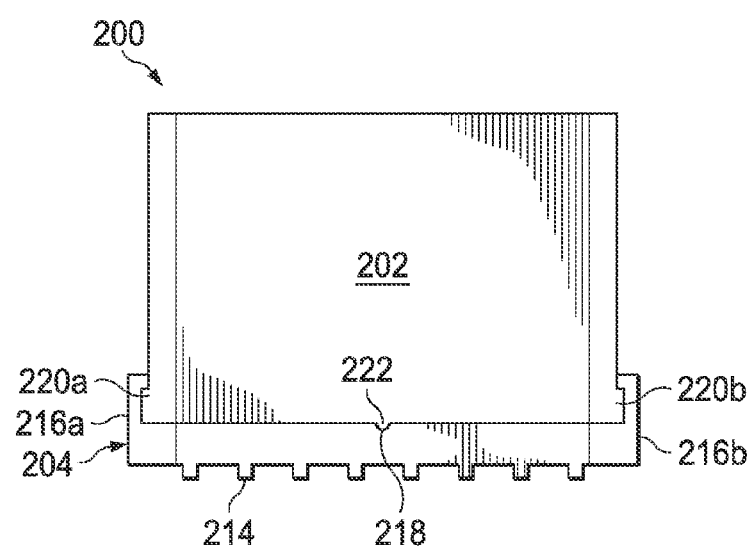
Figure 2C:
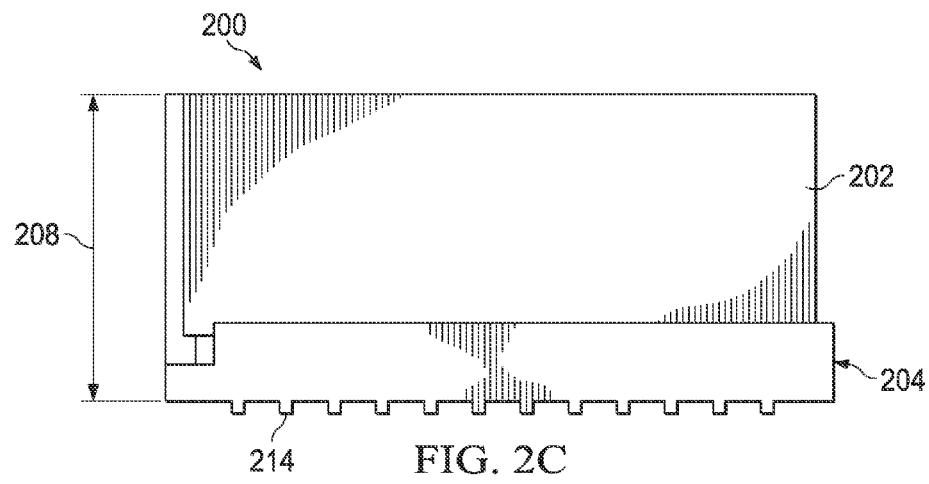
Figure 2D:
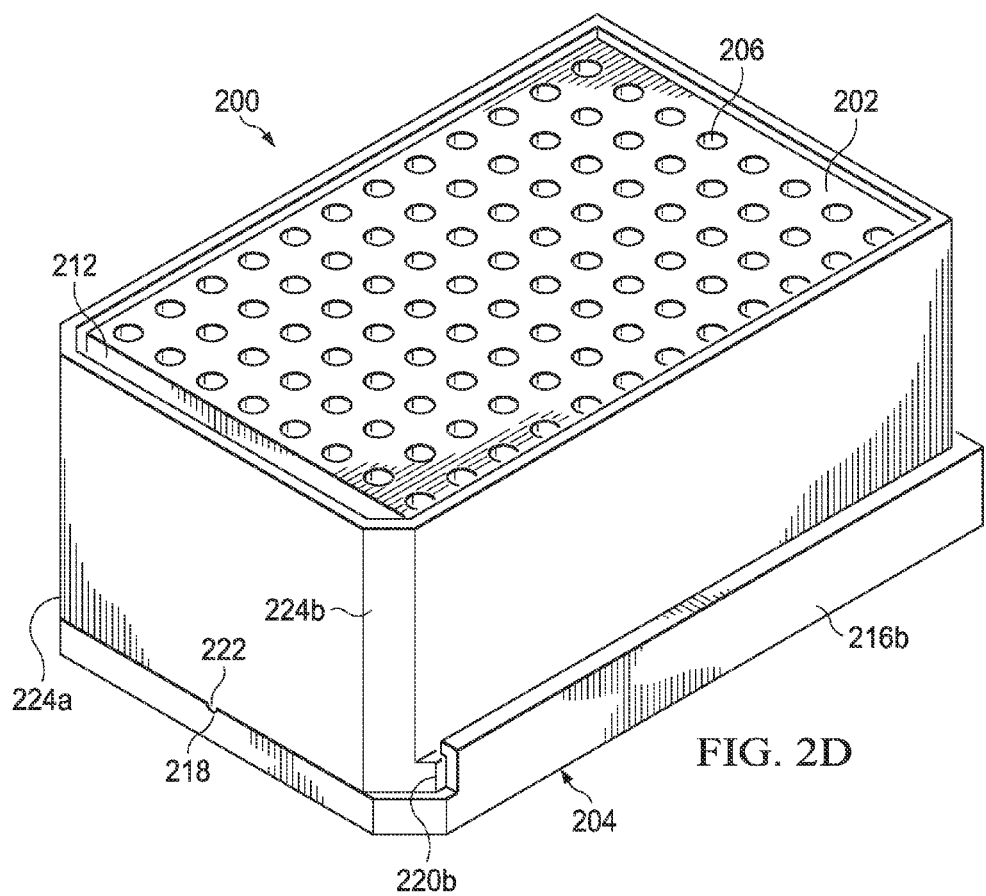

FIGS. 2A-2D illustrate views of an exemplary loading tool for a multi-well chromatography filter plate. FIG. 2A illustrates a top view of loading tool 200, FIGS. 2B and 2C illustrate side views of loading tool 200, and FIG. 2D illustrates a trimetric view of loading tool 200. Loading tool 200 includes top plate 202 and bottom plate 204.

As shown in FIG. 2A, top plate 202 may include multiple wells 206. Wells 206 may have a volume determined by the requirements of the chromatography test, the size of the chromatography testing equipment, and/or the amount of material to be analyzed. For example, wells 206 may have a volume from the microliter scale to the milliliter scale, such as between approximately three hundred microliters to approximately 2.4 milliliters. In some embodiments, height 208, shown in FIG. 2C, may be varied to change the volume of wells 206. In other embodiments, diameter 210 of wells 206, shown in FIG. 2A, may be varied to change the volume of wells 206. While wells 206 are shown in FIGS. 2A-2D as having similar sizes, wells 206 may be of varying sizes. In the illustrated embodiment, loading tool 200 is shown as having ninety-six wells but loading tool 200 may have any number of wells 206 that may be compatible with chromatography testing equipment and/or the requirements of the chromatography test. The number of wells 206 on loading tool 200 may correspond to the number of wells in a multi-well chromatography filter plate (e.g., multi-well chromatography filter plate 432 shown in FIG. 4). For example, multi-well chromatography filter plates may have twelve, twenty-four, forty-eight, ninety-six, or three hundred eighty-four, or any other suitable number of wells 206 depending on the type of chromatography test or assay being performed and the type of chromatography testing or assaying equipment used.

Top plate 202 may further include receptacle 212 that may be used to store excess solid material after the solid material has filled wells 206, as described in further detail below. Material placed in receptacle 212 may be recovered and used in a subsequent chromatography test.

Figure 5:
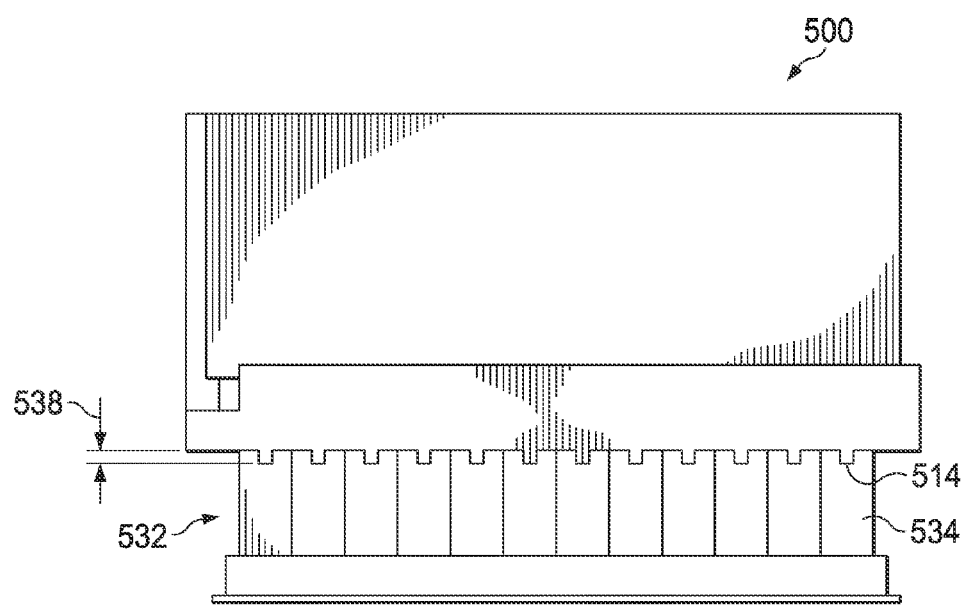
FIG. 5 illustrates a side view of an exemplary loading tool and a multi-well chromatography filter plate prior to loading the multi-well chromatography filter plate.

As shown in FIG. 2C, bottom plate 204 may include multiple funnels 214 that provide a more even, uniform flow of solid material into the multi-well chromatography filter plate. In some embodiments, bottom plate 204 may include the same number of funnels 214 as wells 206 on top plate 202 and/or wells on the multi-well chromatography filter plate. When loading tool 200 is in an empty position, as described in further detail with respect to FIG. 3B, each funnel 214 may align with a single well 206. Funnels 214 may assist in guiding solid material loaded into wells 206 into a multi-well chromatography filter plate (not expressly shown) and may assist a user in aligning loading tool 200 with the multi-well chromatography filter plate as shown in FIG. 5. In some embodiments, funnels 214 may have a similar diameter as wells 206, such as diameter 210, shown in FIG. 2A. In other embodiments, funnels 214 may correspond to the size of the wells of a multi-well chromatography filter plate such that funnels 214 may be seated in the wells of the multi-well chromatography filter plate when loading tool 200 is used to deposit solid material into the multi-well chromatography filter plate. For example, the diameter of the funnels may be sized to fit into the wells of the filter plate and the length of the funnels may be based on the height of the wells of the filter plate, as discussed further with respect to FIG. 5.

Top plate 202 may further include side rails 220a and 220b ("side rails 220") and center rail 222. Bottom plate 204 may further include tracks 216a and 216b ("tracks 216") and keyway 218. Tracks 216 and keyway 218 may be designed such that tracks 216 align with side rails 220 and keyway 218 aligns with center rail 222 to maintain top plate 202 in proper position with respect to bottom plate 204. When assembling loading tool 200, tracks 216 may be inserted into side rails 220 and top plate 202 may slide along side rails 220 relative to bottom plate 204 until a notch (e.g., limiter 326 shown in FIGS. 3A and 3B) engages in a pathway (e.g., pathway 328 shown in FIGS. 3A and 3B). The notch may confine the movement of top plate 202 relative to bottom plate 204 such that the horizontal movement of top plate 202 relative to bottom plate 204 is limited and a single well 206 may be aligned with a single funnel 214. The function of the notch is described in further detail with respect to limiter 326 shown in FIGS. 3A and 3B.

Tracks 216 may be designed to enclose at least three sides of side rails 220 such that top plate 202 and bottom plate 204 may be coupled together to form a single component. The coupling of top plate 202 and bottom plate 204 may allow top plate 202 to slide along track 216 relative to bottom plate 204 and may prevent vertical movement between top plate 202 and bottom plate 204. Thus, loading tool 200 may remain as a single component when loading tool 200 is picked up by a user and may prevent the solid material from exiting wells 206 during transport. Additionally, tracks 216 and/or keyway 218 may confine the movement of top plate 202 to a single plane with respect to bottom plate 204 and prevent top plate 202 and bottom plate 204 from twisting relative to one another.

Figure 4:
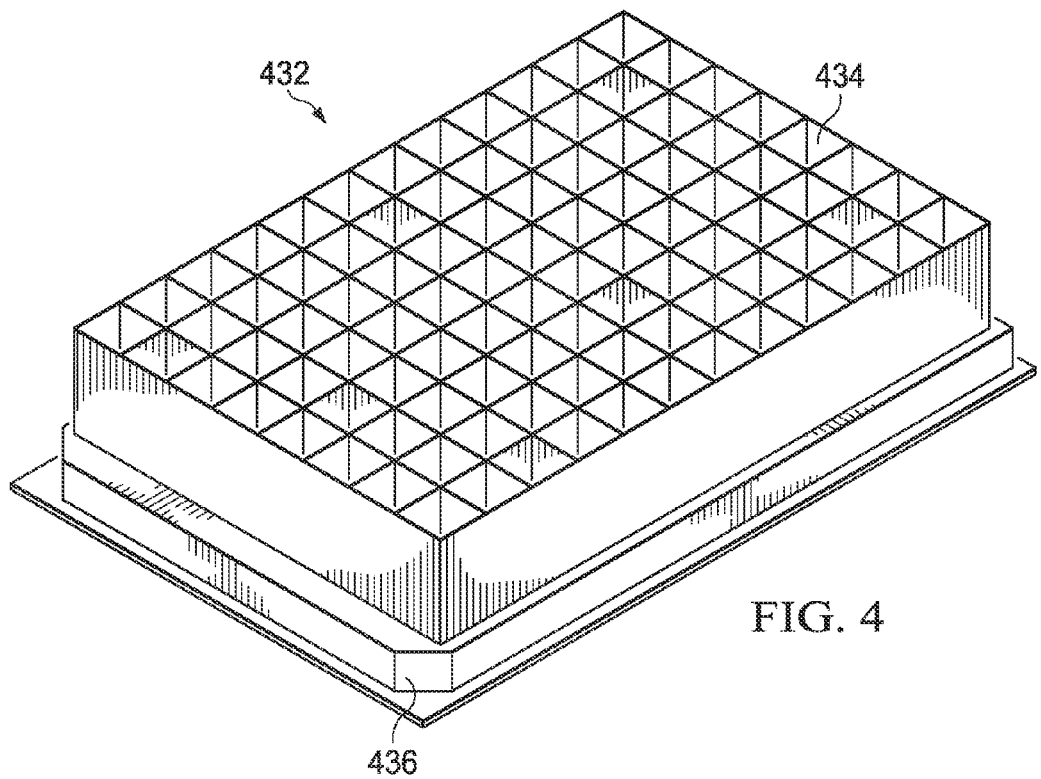
FIG. 4 illustrates a perspective view of a multi-well chromatography filter plate.

In some embodiments, top plate 202 and/or bottom plate 204 may include corners 224a and 224b ("corners 224"), which are notched at an approximately forty-five degree angle to provide a cosmetic and/or visual identifier to a user of the orientation of loading tool 200 and assist a user in lining up loading tool 200 with a multi-well chromatography filter plate that may include notched corners, as described in further detail with respect to FIG. 4. While loading tool 200 is shown as having two notched corners 224, loading tool 200 may include more or fewer notched corners 224.

Top plate 202 and/or bottom plate 204 may be formed of plastic, machined metal such as aluminum or steel, or any other suitable material. In some embodiments, top plate 202 and/or bottom plate 204 may be manufactured by a three-dimensional (3D) printer using a resin plastic or other suitable 3D printer compatible material.

During the use of loading tool 200, a user may load wells 206 of top plate 202 with solid material by pouring solid material onto top plate 202 while top plate 202 is in a loading position. The loading position is described in further detail with respect to FIG. 3A. The solid material may flow into and fill wells 206. After wells 206 are filled with solid material, a user may use a straight edge tool, brush, or any other suitable scraping tool to remove excess solid material from top plate 202 by scraping the tool across top plate 202 while leaving the solid material in wells 206 undisturbed. The scraping tool may be used to level the volume of solid material in multiple wells 206 at approximately the same time. In some embodiments, the excess solid material may be scraped from top plate 202 and placed in receptacle 212.

Figure 3A:
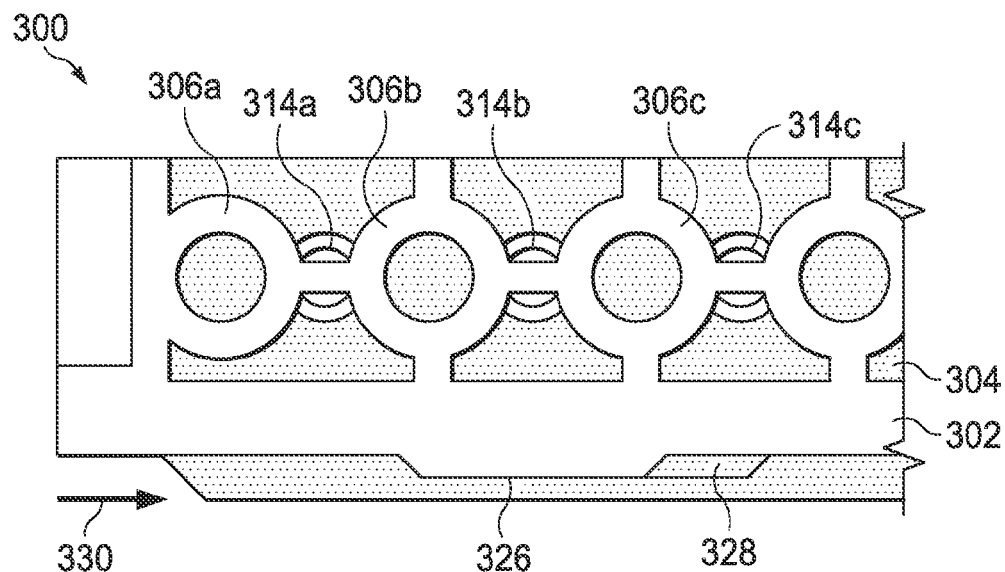
FIG. 3A illustrates a bottom view of an exemplary loading tool for a multi-well chromatography filter plate in a loading position.

FIG. 3A illustrates a bottom view of an exemplary loading tool for a multi-well chromatography filter plate in a loading position. In the loading position, wells 306a-306c ("wells 306") are offset from funnels 314a-314c ("funnels 314") such that the solid material loaded in wells 306 may not flow out of wells 306 and through funnels 314.

Loading tool 300 may feature limiter 326 and pathway 328 that may limit the movement of top plate 302 relative to bottom plate 304. Limiter 326 may be a notch formed in a side rail, such as side rail 220 shown in FIGS. 2A-2D and pathway 328 may be formed in a track, such as track 216 shown in FIGS. 2A-2D. In the loading position, limiter 326 may be at one end of pathway 328 such that wells 306 and funnels 314 are offset and solid material cannot exit wells 306. In other embodiments, limiter 326 and pathway 328 may be a component of a center rail and a keyway, respectively. For example, limiter 326 may be a part of center rail 222 and pathway 328 may be a part of keyway 218, shown in FIGS. 2B and 2D.

Figure 3B:
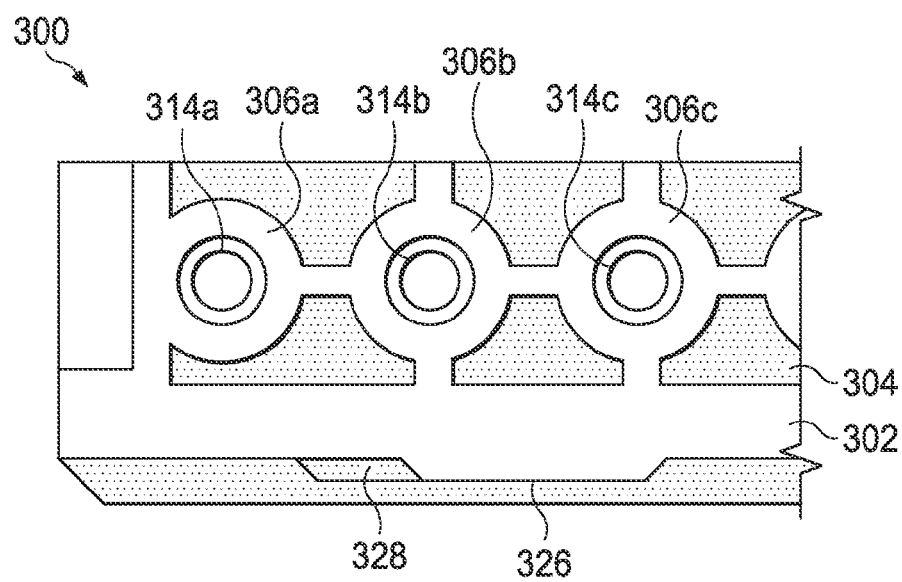
FIG. 3B illustrates a bottom view of an exemplary loading tool for a multi-well chromatography filter plate in an empty position.

FIG. 3B illustrates a bottom view of an exemplary loading tool for a multi-well chromatography filter plate in an empty position. During use, while loading tool 300 is positioned over the top of a multi-well chromatography filter plate, such as multi-well chromatography filter plate 432 shown in FIG. 4, top plate 302 may slide across bottom plate 304, along tracks, such as tracks 216 shown in FIGS. 2A-2D, into the empty position. In the empty position wells 306 may be aligned with funnels 314. The alignment of wells 306 and funnels 314 may allow the solid material to flow from wells 306, through funnels 314, and into the wells of a multi-well chromatography filter plate.

While loading tool 300 is positioned over the top of a multi-well chromatography filter plate, limiter 326 may be moved in direction 330 along pathway 328 to an empty position where wells 306 are aligned with funnels 314 and the solid material loaded in wells 306 may flow through funnels 314. The combination of limiter 326 and pathway 328 may limit the movement of top plate 302 such that wells 306 and funnels 314 have a one-to-one relationship, e.g., the contents of a single well 306 may only flow through a single funnel 314. For example, the contents of well 306a may flow only through funnel 314a. Limiter 326 and pathway 328 may reduce user error when loading and using a multi-well chromatography filter plate. For example, limiter 326 and pathway 328 may prevent overloading and/or underloading of the wells of a multi-well chromatography filter plate caused by a user sliding top plate 302 too far or too little in either direction with respect to bottom plate 304.

In some embodiments, limiter 326 may be moved in pathway 328 to an intermediate position (e.g., any position between the loading position and the empty position). By moving limiter 326 to an intermediate position, a user may control the flow rate of the solid material through funnels 314. When limiter 326 is in an intermediate position, wells 306 and funnels 314 may maintain a one-to-one relationship and the restricted flow rate through each funnel 314 may remain the same relative to other funnels 314.

The flow rate of solid material from wells 306 through funnels 314 may be controlled by the diameter of funnels 314. In certain embodiments, all funnels on bottom plate 304 may have the same diameter. Therefore, each well of the multi-well chromatography filter plate may receive the same amount of solid material due to all funnels 314 being opened simultaneously and for the same amount of time as a user slides top plate 302 from the loading position to the empty position, resulting in decreased error and variability in the results of the chromatography analysis that may be caused by differences in the loading of the solid material. Additionally, the solid material may flow at the same rate into each well of the multi-well chromatography filter plate and may result in more consistent solid packing from well to well of the multi-well chromatography filter plate than may be achieved when each well is filled individually at varying flow rates.

After solid material has flowed into the wells of the multi-well chromatography filter plate, loading tool 300 may be removed from the top of the multi-well chromatography filter plate and the multi-well chromatography filter plate may be used in any appropriate chromatography application, e.g., testing related to subterranean operations, pharmaceutical or biotechnology testing, or any other high-throughput chromatography application.

FIG. 4 illustrates a perspective view of a multi-well chromatography filter plate. Multi-well chromatography filter plate 432 may include multiple wells 434 that may be filled with a liquid and/or a solid material and used to perform chromatography testing. While multi-well chromatography filter plate 432 is shown as having ninety-six wells 434, multi-well chromatography filter plate 432 may include any number of wells 434. For example, multi-well chromatography filter plates may have twelve, twenty-four, forty-eight, ninety-six, or three hundred eighty-four wells 206 depending on the type of chromatography test being performed and the type of chromatography testing equipment used.

Multi-well chromatography filter plate 432 may include one or more notched corners 436. A loading tool (e.g., loading tool 200 shown in FIGS. 2A-2D) may be aligned with multi-well chromatography filter plate 432 by aligning notched corners 436 with one or more notched corners on the loading tool, such as notched corners 224 shown in FIGS. 2A-2D.

FIG. 5 illustrates a side view of an exemplary loading tool and a multi-well chromatography filter plate prior to loading the multi-well chromatography filter plate. Loading tool 500 may be aligned with multi-well chromatography filter plate 532 such that one funnel 514 is aligned in one and only one well 534 of the multi-well chromatography filter plate 532 while loading multi-well chromatography filter plate 532.

Funnels 514 may extend out from loading tool 500 and into wells 534 of multi-well chromatography filter plate 532 by length 538 to enable each of funnels 514 to direct solid material into a single well 534 and avoid solid material flowing from one funnel 514 into more than one well 534. Additionally, length 538 of funnels 514 may be a length that may prevent any pre-loaded fluid in wells 534 from being wicked upwards into funnel 514. The wicking of pre-loaded fluid into funnel 514 may cause clogs to form in funnel 514.

While loading tool 500 is positioned above multi-well chromatography filter plate 532, loading tool 500 may be moved from a loading position to an empty position where solid material may flow from the wells of loading tool 500 through funnels 514 into the wells 534. The movement of loading tool 500 may be limited by a limiter (e.g., limiter 326 shown in FIGS. 3A and 3B) such that the flow through a single funnel 514 may be directed only to a single well 534. This may prevent overloading and/or underloading of the wells of a multi-well chromatography filter plate caused by solid material flowing from one funnel 514 into more than one well 534.

Embodiments disclosed herein include:

A. A loading tool for loading material for chromatography testing including a top plate and a bottom plate. The top plate includes a plurality of wells for holding a material, a rail located along a side of the top plate, and a notch formed in the rail. The bottom plate is slidably coupled to the top plate and includes a plurality of funnels extending from the bottom plate, each of the plurality of funnels corresponding to one of the plurality of wells, a track located along a side of the bottom plate to receive the rail located on the top plate, and a pathway formed in the track to receive the notch such that the notch and the pathway limit movement of the top plate relative to the bottom plate.

B. A method for loading material for chromatography testing including placing a material on a top plate of a loading tool while the top plate is in a loading position. The top plate includes a plurality of wells for holding the material, a rail located along a side of the top plate, and a notch formed in the rail. The method further includes scraping a tool across the top plate to remove excess material after the material fills the plurality of wells, placing the loading tool over a multi-well chromatography filter plate, and sliding the top plate of the loading tool from the loading position to an empty position, the empty position allowing the material to flow into the filter plate from the top plate through a bottom plate. The bottom plate is slidably coupled to the top plate and includes a plurality of funnels extending from the bottom plate, each of the plurality of funnels corresponding to one of the plurality of wells, a track located along a side of the bottom plate to receive the rail located on the top plate, and a pathway formed in the track to receive the notch such that the notch and the pathway limit movement of the top plate relative to the bottom plate.

C. A system for loading material for chromatography testing including a chromatography filter plate including a first plurality of wells and a loading tool for loading a material into the chromatography filter plate. The loading tool includes a top plate and a bottom plate. The top plate includes a second plurality of wells for holding a material, a rail located along a side of the top plate, and a notch formed in the rail. The bottom plate is slidably coupled to the top plate and includes a plurality of funnels extending from the bottom plate, each of the plurality of funnels corresponding to one of the second plurality of wells, a track located along a side of the bottom plate to receive the rail located on the top plate, and a pathway formed in the track to receive the notch such that the notch and the pathway limit movement of the top plate relative to the bottom plate.

Each of embodiments A, B, and C may have one or more of the following additional elements in any combination. Element 1: wherein the top plate further includes a center rail and the bottom plate further includes a keyway to receive the center rail. Element 2: wherein the top plate further includes a receptacle for storing excess material. Element 3: wherein the plurality of funnels extend from the bottom plate and have a length that prevents wicking of a pre-loaded fluid from a chromatography filter plate into at least one of the plurality of funnels. Element 4: wherein the plurality of funnels extend from the bottom plate and have a length that prevents a material from flowing into more than one well on the chromatography filter plate. Element 5: wherein the volume of at least one of the plurality of wells is different from the volume of another of the at least one of the plurality of wells. Element 6: wherein at least one of the top plate or the bottom plate is manufactured by a three-dimensional (3D) printer. Element 7: wherein scraping the tool across the top plate further includes sweeping excess material into a receptacle on the top plate. Element 8: wherein a volume of the plurality of wells is changed by changing a height of the top plate.

Although the present disclosure has been described with several embodiments, various changes and modifications may be suggested to one skilled in the art. For example, although the present disclosure describes a loading tool to load solid material into a multi-well chromatography filter plate, the same principles may be used to load liquid material according to the present disclosure. For example, the loading tool may be used to simultaneously add liquid to each well of the multi-well chromatography filter plate. In embodiments loading liquid material, the loading tool may additionally include seals to prevent the liquid material from leaking out of the wells of the loading tool. Additionally, while the loading tool is described as being used for high-throughput chromatography systems, the loading tool may be used with solid-phase extraction (SPE) systems or other systems involving multi-well plates (e.g., other filter, collection, reaction block, or storage type plates). It is intended that the present disclosure encompasses such changes and modifications as fall within the scope of the appended claims.

What is claimed is:

1. A loading tool for loading material for chromatography testing comprising:
    a top plate including:
        a plurality of wells for holding a material;
        a rail located along a side of the top plate; and
        a notch formed in the rail; and
    a bottom plate slidably coupled to the top plate, the bottom plate including:
        a plurality of funnels extending from the bottom plate, each of the plurality of funnels corresponding to one of the plurality of wells;
        a track located along a side of the bottom plate to receive the rail located on the top plate; and
        a pathway formed in the track to receive the notch such that the notch and the pathway limit movement of the top plate relative to the bottom plate between a loading position and an empty position.

2. The loading tool of claim 1, wherein:
the top plate further includes a center rail; and
the bottom plate further includes a keyway to receive the center rail.

3. The loading tool of claim 1, wherein the top plate further includes a receptacle for storing excess material.

4. The loading tool of claim 1, wherein the volume of at least one of the plurality of wells is different from the volume of another of the at least one of the plurality of wells.

5. The loading tool of claim 1, wherein at least one of the top plate or the bottom plate is manufactured by a three-dimensional (3D) printer.

6. A system for loading material for chromatography testing comprising:
    a chromatography filter plate including a first plurality of wells; and
    a loading tool for loading a material into the chromatography filter plate, the loading tool including:
        a top plate including:
            a second plurality of wells for holding a material;
            a rail located along a side of the top plate; and
            a notch formed in the rail; and
        a bottom plate slidably coupled to the top plate, the bottom plate including:
            a plurality of funnels extending from the bottom plate, each of the plurality of funnels corresponding to one of the second plurality of wells;
            a track located along a side of the bottom plate to receive the rail located on the top plate; and
            a pathway formed in the track to receive the notch such that the notch and the pathway limit movement of the top plate relative to the bottom plate between a loading position and an empty position.

7. The system of claim 6, wherein:
the top plate further includes a center rail; and
the bottom plate further includes a keyway to receive the center rail.

8. The system of claim 6, wherein the top plate further includes a receptacle for storing excess material.

9. The system of claim 6, wherein the volume of at least one of the second plurality of wells is different from the volume of another of the at least one of the second plurality of wells.

* * * * *